(12) United States Patent
Coutts et al.

(10) Patent No.: US 6,603,993 B1
(45) Date of Patent: Aug. 5, 2003

(54) ENDOSCOPE SUITABLE FOR MAGNETIC RESONANCE IMAGING

(75) Inventors: Glyn A Coutts, London (GB); David James Larkman, London (GB); David John Gilderdale, South Devon (GB); Anthony Charles Grantham, Surrey (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 203 days.

(21) Appl. No.: 09/716,162

(22) Filed: Nov. 17, 2000

(30) Foreign Application Priority Data

Nov. 19, 1999 (GB) .............................. 9927358

(51) Int. Cl.[7] .................................. A61B 5/05
(52) U.S. Cl. ................... 600/423; 600/410; 600/419
(58) Field of Search .................. 600/423, 101, 600/139, 149, 410, 146, 148, 435; 324/318

(56) References Cited

U.S. PATENT DOCUMENTS

| 4,616,631 A | * 10/1986 | Takahashi ................... 600/139 |
| 4,960,106 A | 10/1990 | Kubokawa et al. |
| 5,035,231 A | 7/1991 | Kubokawa et al. |
| 5,427,103 A | 6/1995 | Fujio et al. |
| 5,738,632 A | * 4/1998 | Karasawa ................... 600/410 |
| 5,752,912 A | * 5/1998 | Takahashi et al. .......... 600/419 |
| 5,876,338 A | 3/1999 | Gilderdale et al. |
| 6,228,055 B1 | * 5/2001 | Foerster et al. ............. 604/116 |

FOREIGN PATENT DOCUMENTS

| EP | 0 165 718 | 12/1985 |
| EP | 0 301 288 | 7/1988 |
| GB | 2 343 251 A | 3/2000 |
| JP | 8-84718 | 4/1996 |
| JP | 11-225984 | 8/1999 |
| WO | WO 99/18852 | 4/1999 |

OTHER PUBLICATIONS

C.L. Dumoulin, et al.; "Real–Time Position Monitoring of Invasive Devices Using Magnetic Resonance," *MRM* 29:411–415 (1993).

* cited by examiner

*Primary Examiner*—Quang T. Van
(74) *Attorney, Agent, or Firm*—Thomas M. Lundin

(57) ABSTRACT

In an endoscope, the tip which contains passages for viewing and light guiding is made of plastics material, for MR compatibility purposes, and an r.f. receive coil of the endoscope is provided with a fiducial having its own r.f. receive coil, to make it possible to track movement of the r.f. receive coil.

18 Claims, 4 Drawing Sheets

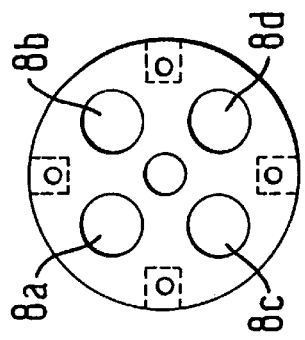
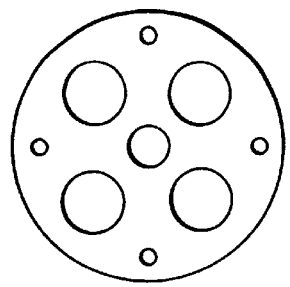
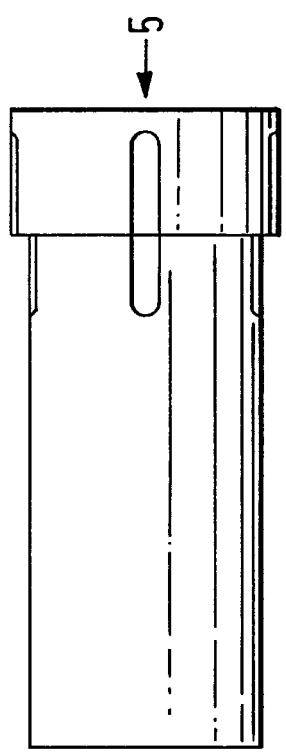
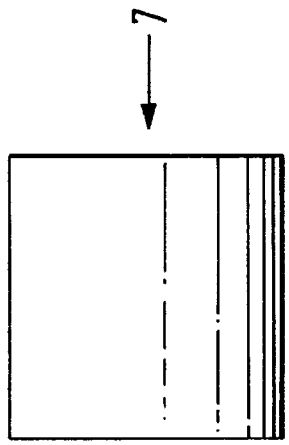

ENDOSCOPE SUITABLE FOR MAGNETIC RESONANCE IMAGING

BACKGROUND

This invention relates to endoscopes suitable for magnetic resonance (MR) imaging.

Endoscopes are medical instruments suitable for insertion into a body cavity, and may include a viewing system, a light guide, an opening for injecting air or water, an opening to which a vacuum can be applied, and an opening for tools etc.

Endoscopes are usually in the form of flexible tubes which have axial passages for cables with which the tip of the endoscope may be steered, as well as for the services referred to in the preceding paragraph. In one construction, a series of outwardly-dished disks are contained in a sheath (EP-A-0 165 718).

While endoscopes produce visible images of the interior of the cavities under investigation, medical examination often requires an image of the tissue behind the tip of the endoscope. For this reason, it has been proposed to provide endoscopes with MR receive coils, in order to acquire MR signals with reasonably high signal-to-noise ratio from the tissue in the immediate vicinity of the endoscope (EP-A-0 850 595).

Such endoscopes are not at the present time commercially available, because of two principal difficulties in implementing such devices.

The first difficulty is that a conventional endoscope typically includes metals e.g. stainless steel for the steering cables, a metallic flat wire spiral for the sheath. Such materials would distort the powerful main magnetic field which underlies MR imaging, and hence the resulting MR image produced would be distorted. Secondly, currents, detrimental to the patient, would be induced in such materials when the r.f. excitation pulse, used to excite the resonance, was applied.

The second difficulty is that such an endoscope may not be fixed in position when the MR image is being built up. For example, the endoscope could be within a stomach cavity, and involuntary muscular movement of the walls could cause the endoscope to move around. An MR image requires collection of information over a period of time. For example, in order to spatially encode a two-dimensional slice, a series of r.f. excitations takes place, after each of which a phase-encode magnetic field gradient of a different magnitude is applied before a read-out pulse in the presence of an orthogonal magnetic field gradient, takes place. Any movement of the r.f. receive coil during the data collection would cause artifacts to appear in the MR image, which is calculated on the assumption that the r.f. receive coil remains fixed in position relative to the tissue during the building up of the MR image from the various pulses corresponding to the respective phase-encode gradients.

SUMMARY

The invention provides an endoscope which includes an r.f. receive coil, wherein the tip of the endoscope which contains passages for viewing means and light guide means is made of plastics material, and wherein a bendable portion of the endoscope connected to the tip includes disks of plastics material inside a sleeve of non-metallic material, the disks having openings through which steering cables of non-metallic material pass.

Such an endoscope is MR compatible, in the sense that the materials do not interfere with the main magnetic field, nor create current inducing loops.

The tip of the endoscope may be made from polyether etherketone (PEEK). The sleeve and/or the steering cable may be made from polyethylene (for example Dyneema, made by DSM High Performance Fibers B.V., Holland, a high performance gel spun polyethylene fiber), glass, carbon, nylon (a family of polyamide polymers) or aramid (a class of aromatic polyamide fibres, such as Kevlar or Twaron).

The bendable portion of the endoscope is connected to a flexible portion, for insertion into the patient. This insertion portion may be connected by a non-metallic umbilical, of at least 2½ metres, preferably at least 4 metres in length, to a services cabinet.

The invention also provides an endoscope which includes an r.f. receive coil, and a fiducial fixed relative to the r.f. receive coil which is provided with its own r.f. receive coil.

It then becomes possible to track the movement of the r.f. receive coil so that movement of the r.f. receive coil can be compensated for when building up the MR image.

DRAWINGS

One way of carrying out the invention will now be described in greater detail, by way of example, with reference to the accompanying drawings, in which:

FIG. 4 is a side view of the tip of the endoscope;

FIG. 5 is an end view of the tip taken through the section 5,5 of FIG. 4;

FIG. 6 is a side view of a central anchor region of the endoscope;

FIG. 7 is a sectional view taken along the lines 7,7 on FIG. 6;

DESCRIPTION

Figure 1:
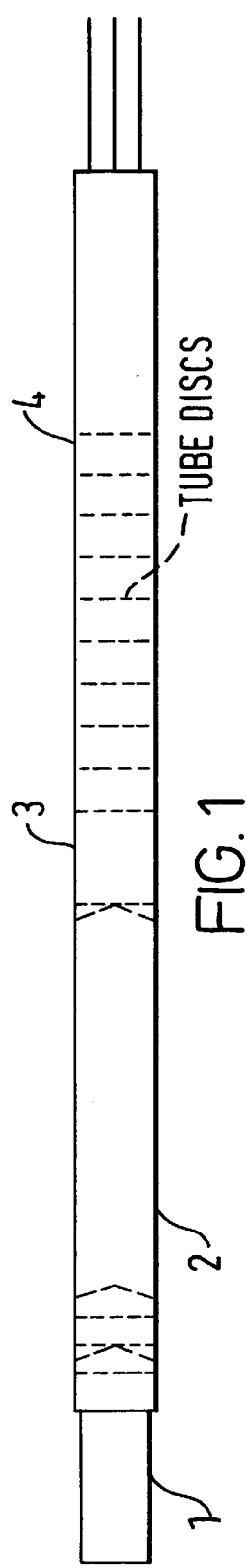
FIG. 1 is a schematic side view of an endoscope in accordance with the invention.

The endoscope consists of a main insertion tube, a proximal body portion (not shown), an umbilical (not shown), and a connector to a services cabinet (not shown).

The umbilical is constructed of non-metallic materials like the insertion tube, and is 5 metres long, in order that the services cabinet, which will generally be metallic, can be kept well away from the magnetic resonance imaging apparatus, to which the receive coil of the endoscope is connected.

The proximal body portion is made of polyurethane mouldings, and is rigid plastics material, and contains the control knob used to steer and control the endoscope.

The insertion tube consists of a distal tip 1, a steerable bendable section 2, and a main bendable but not steerable insertion tube 4. The section 2 and the section 4 are connected by a spiral anchor 3.

Figure 2:
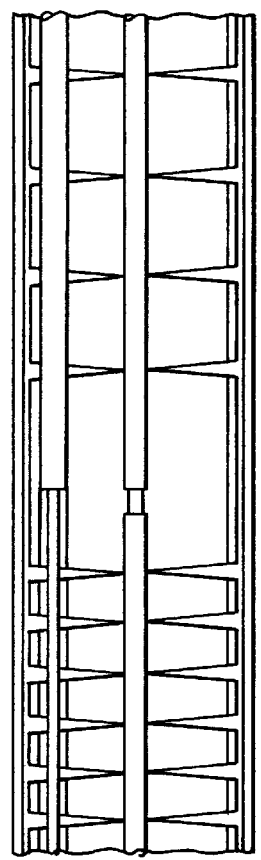
FIG. 2 is an axial section of the front part of the endoscope of FIG. 1.
Figure 3:
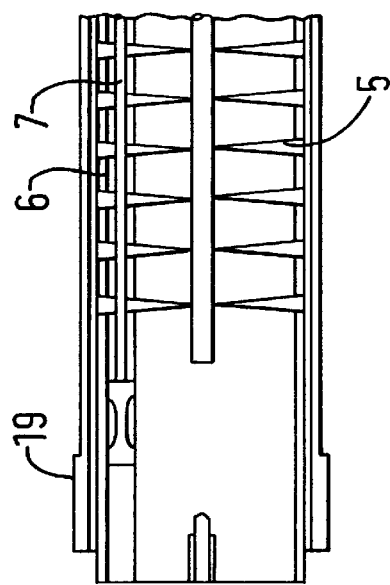
FIG. 3 is an axial sectional view of a part of the central region of the endoscope shown in FIG. 1.

The distal tip is made of plastics material, in fact, polyether etherketone (PEEK), in contrast to conventional endoscopes in which the tip is made of stainless steel. The steerable section comprises a number of dished-disks 5 which are apertured at 6 to receive steering cables 7 (only one of which is shown in FIG. 2 although four or five are provided. The dished-disks could be similar to those shown in FIGS. 5A and 5B of EP-A-0 165 718. The disks are made of plastics material, for example, of PEEK although nylon or acetal could be used. The steering cable may be of nonmetallic material, in place of the conventional stainless steel. The steering cable is contained within a nickel alloy sheath for example, Cromaloy. The spiral anchor 3 is also made of plastics material such as PEEK, and the bendable main insertion tube 4 is also composed of plastics disks having openings through which the steering cable passes. These plastics disks are made of acetal, such as DELRIN, but nylon or PEEK could be used.

The spiral anchor is the junction piece between the steerable section 2 and the non-steerable flexible section 4. It is used to anchor the outer casings of the steering cables, which thus act as Bowden cables. The casings of the steering cables are spirally wound to form the casings, and are made of Cromaloy. The cables themselves are anchored to the distal tip 1. Manipulation of controls on the proximal body portion cause the steerable portion 2 to steer in the desired way.

The steering cable may be made of polyethylene, such as Dyneema, a high performance gel spun polyethylene fiber, but could instead be made of glass, carbon, nylon or aramid.

The disks are contained in two sleeves, an inner sleeve of non-metallic braid for example Aramid to give it torsional rigidity, in place of the stainless steel or copper braid which has hitherto been used to give the insertion tube its torsional rigidity. The endoscope has an outer sleeve of non-metallic material such as EPDM (Ethylene propylene Diene Modified) over the steerable section 2 and an outer sleeve of flexible polyurethane over the insertion tube portion 4. The inner sleeves could instead consist of fabric made of glass, carbon or nylon or polyethylene such as Dyneema.

Referring to FIGS. 4 and 5, the distal tip 1 of the endoscope has apertures 8a to 8d at its inner end to receive the service modules shown in FIGS. 8 to 11, and these communicate with openings (not shown) in the distal end of the distal tip.

Figure 8:
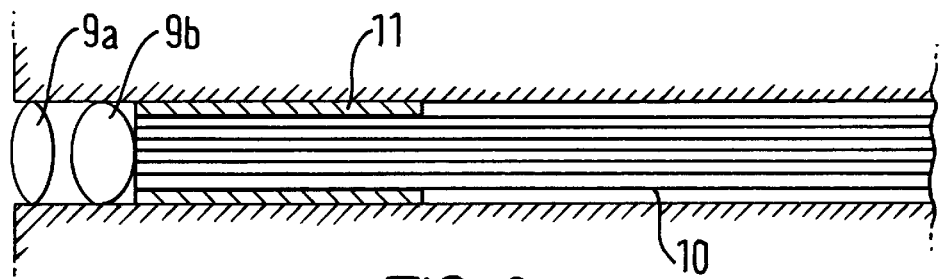
FIG. 8 is a sectional view of a light guide opening into the end of the tip.
Figure 9:
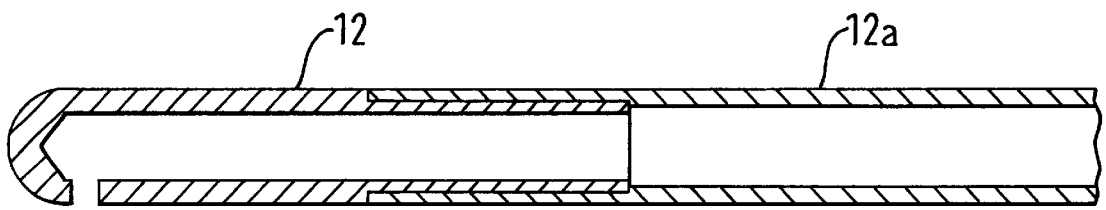
FIG. 9 is a sectional view of an air/water inlet which opens at the end of the tip.

The light guide shown in FIG. 8 comprises lenses 9a, 9b to spread light sent along glass fibres 10 which are clamped in ferrule 11 of plastics material such as PEEK. The air/water channel shown in FIG. 9 provides a jet for cleaning the lens shown in FIG. 8 and the possibility of air to inflate a body cavity into which the endoscope is inserted. The hollow end 12 of the module shown in FIG. 9 is made of plastics material such as PEEK, connected to a tube 12a of EVA (ethylene-vinyl acetate copolymer).

Figure 10:
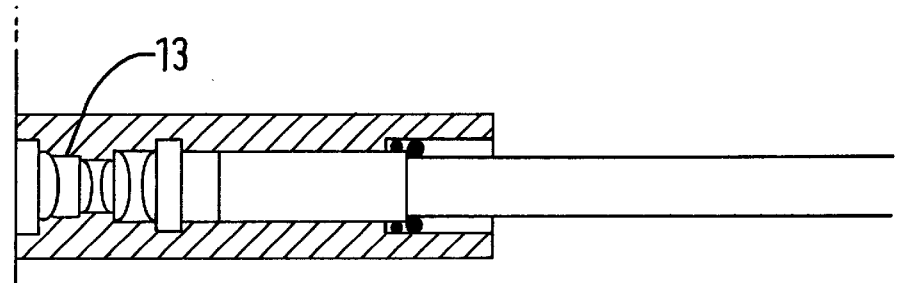
FIG. 10 is an axial section of a viewing window which opens at the end of the tip.

The viewer shown in FIG. 10 comprises lenses and spacers 13 potted in Araldite within a ferrule of silicon brass in a channel of the distal tip.

Figure 11:
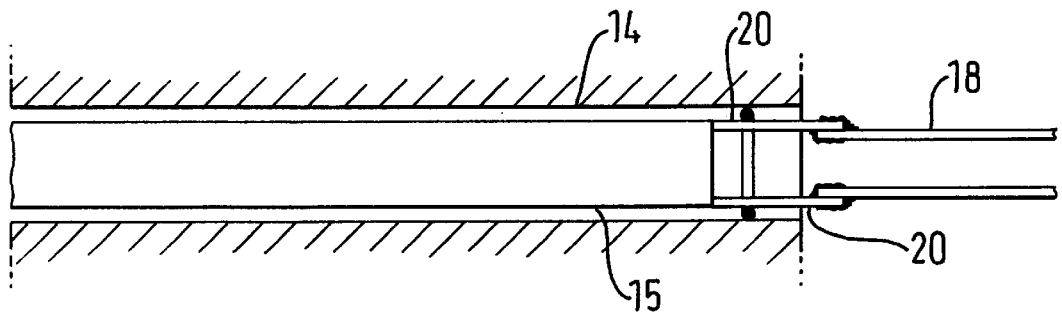
FIG. 11 is a sectional view of a cavity for an MR pick-up coil which opens at the end of the tip.

Referring to FIG. 11, the r.f. pick-up coil accommodated in this cavity 14 in the distal end of the distal tip is not shown, but the former 15 on which the r.f. pick-up coil is mounted is shown schematically.

The r.f. pick-up coil on its former 15 is inserted into the cavity 14 and sealed in position by means of O-rings. The r.f. pick-up coil mounted on the former inductively couples to an r.f. receive coil 19 (FIG. 2) which surrounds the outer periphery of the end of the distal tip 1, in the manner shown in EP-A-0 850 595.

Thus, r.f. signals detected by the r.f. receive coil surrounding the distal tip 1 induce signals in the r.f. pick-up coil mounted on former 15 and these signals are then transmitted via silicon brass pins 20 araldited into PEEK, along wires 18 back along the length of the endoscope which is then connected to one channel of magnetic resonance imaging apparatus.

In accordance with another aspect of the invention (FIGS. 11 to 13), a fiducial 17 including an MR visible sample is mounted on the former 15, and the fiducial 17 is surrounded by an r.f. receive coil 16 which is also connected to the MR imaging apparatus via wires 21 extending along the service channel, but in this case a separate channel of the magnetic resonance imaging apparatus.

The fiducial coil 16 is mounted with its axis transverse to the long axis of the endoscope. It is thus orthogonal to the pick-up coils 15a, and orthogonal also to the receive coil 19, so that there is the minimum of coupling between the coil 16 on the one hand and the coils 15a and 19 on the other hand.

Figure 12:
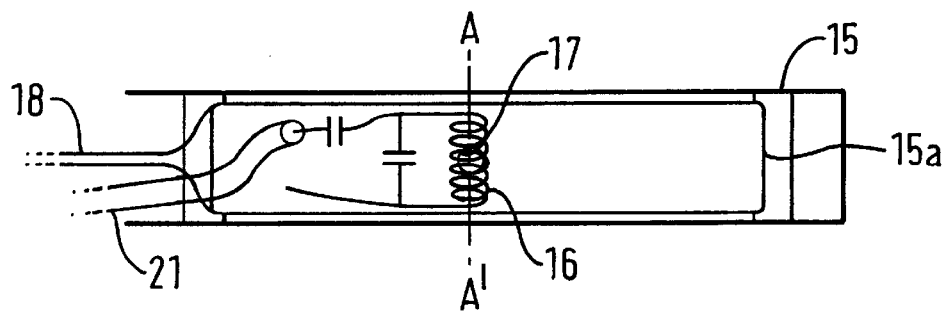
FIG. 12 shows the former 15 of FIG. 11 bearing the pick-up coil and fiducial coil.
Figure 13:
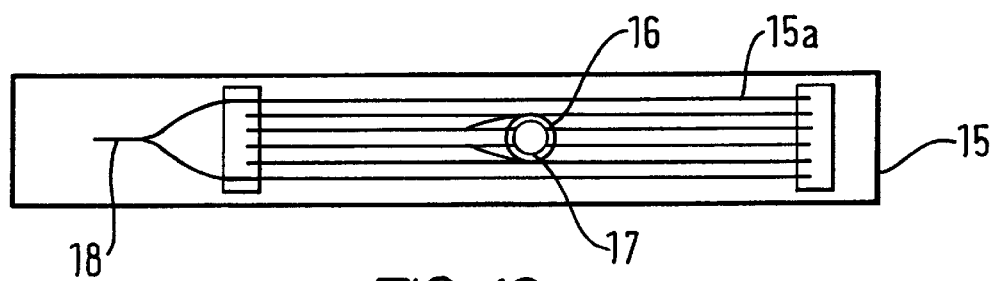
FIG. 13 is a top view along the line A—A' in FIG. 12.

The assembly shown in FIGS. 12 and 13 is inserted into the cavity 14 from the open end with the cables 18, 21 on the side of the former first to enter the cavity. Other sitings of the fiducial and its coil within the cavity 14 are of course possible.

The r.f. pulse sequence of the magnetic resonance imaging apparatus is such that each r.f. excitation pulse for exciting the tissue to be imaged may be accompanied by one or more further pulses of small flip angle which do not therefore excite the tissue to any great extent but which do excite the magnetic resonant active fiducial 17. Thus, when the r.f. receive coil surrounding the distal tip collects an echo signal, a signal is also collected by the receive coil 16. Alternatively, the fiducial may be excited as described in UK Patent Application GB 2343251A (title: MRI gradient field probe; inventors: M. Burl and J. R. Young,) or may use the main excitation and/or similar pulses, instead of having a separate excitation pulse.

In fact, magnetic field gradients are applied in such a way as to spatially locate in the co-ordinate system of the MR imaging apparatus the fiducial, for each r.f. pulse applied to excite the tissue to be imaged. Three gradients may be applied one at a time, to locate the fiducial, as described by Dumoulin et al Magn Resonance Med 1993 29 411 if all these dimensions of its location have to be measured. In other instances, one dimension only may be needed, and the same r.f. pulse as is used to excite the tissue to be imaged can be used for the fiducial also.

Thus, in the processing of the r.f. information received concerning the tissue, a correction can be built in to reflect the movement undergone by the r.f. receive coil 19 as monitored by the fiducial 17.

This then reduces or eliminates motion artifacts concerned with movement of the endoscope during data collection.

The tissue to be imaged may be excited by a coil surrounding the body of the person into whom the endoscope is being inserted, but the r.f. pick-up coil mounted on the former 15 could also operate to cause the r.f. coil 19 surrounding the distal tip to operate in a transmit sense as well as in a receive sense.

Equally, while the coil 16 surrounding the fiducial 17 could be receive only, it could if desired be transmit and receive.

The endoscope may be a colonoscope, laparascope, cystoscope, or gastroscope, or other type of endoscope.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof.

What is claimed is:

1. An endoscope for use in magnetic resonance imaging, the endoscope comprising:
   a distal portion comprised of a non-metallic material and formed such that a plurality of passages are defined therethrough;
   an r.f. receive coil disposed at the distal portion;
   a steerable flexible section connected to the distal portion, the steerable flexible section comprised of a non-metallic material and formed such that a plurality of passages are defined therethrough;
   a plurality of cables comprised of a non-metallic material and connected to the distal portion, for steering the endoscope; and
   a fiducial marker disposed at the distal portion and a fiducial r.f coil surrounding the fiducial marker.

2. The endoscope as claimed in claim 1 further comprising:
   a non-steerable flexible section, the non-steerable flexible section comprised of a non-metallic material and formed such that a plurality of passages are defined therethrough; and
   a spiral anchor for connecting the non-steerable flexible section to the steerable flexible section, the spiral anchor comprised of a non-metallic material and formed such that a plurality of passages are defined therethrough.

3. The endoscope as claimed in claim 2 wherein the non-steerable flexible section further comprises a plurality of dish-shaped disks comprised of a non-metallic material and formed such that a plurality of passages are defined therethrough.

4. The endoscope as claimed in claim 3 wherein the dish-shaped disks are formed from a material selected from the group consisting of polyether etherketone, nylon, and acetal.

5. The endoscope as claimed in claim 1 wherein the distal portion comprises polyether etherketone.

6. The endoscope as claimed in claim 1 wherein the steerable flexible section further comprises a plurality of dish-shaped disks comprised of a non-metallic material and formed such that a plurality of passages are defined therethrough.

7. The endoscope as claimed in claim 6 wherein the dish-shaped disks are formed from a material selected from the group consisting of polyether etherketone, nylon, and acetal.

8. The endoscope as claimed in claim 1 wherein the cables are formed from a material selected from the group consisting of polyethelene, glass, carbon, nylon, and aramid.

9. The endoscope as claimed in claim 1 further comprising an r.f. pickup coil disposed at the distal portion and inductively coupled to the r.f. receive coil.

10. The endoscope as claimed in claim 1 wherein the endoscope has a longitudinal axis and the fiducial r.f. coil defines a fiducial coil axis and the fiducial r.f. coil is disposed at the distal portion such that the fiducial coil axis is orthogonal to the longitudinal axis of the endoscope.

11. The endoscope as claimed in claim 10 further comprising means for tracking movement of the r.f. receive coil and means for correcting magnetic resonance image artifacts due to the movement of the r.f. receive coil.

12. The endoscope as claimed in claim 1 wherein the r.f. receive coil is also a transmit coil.

13. An endoscope for use in magnetic resonance imaging, the endoscope comprising:
    a distal portion;
    an r.f. receive coil disposed at the distal portion;
    a fiducial marker disposed at the distal portion in a fixed spatial relationship to the r.f. receive coil; and
    a fiducial r.f. coil surrounding the fiducial marker.

14. The endoscope as claimed in claim 13 further comprising an r.f. pickup coil disposed at the distal portion and inductively coupled to the r.f. receive coil.

15. The endoscope as claimed in claim 13 wherein the endoscope has a longitudinal axis and the fiducial r.f. coil defines a fiducial coil axis and the fiducial r.f. coil is disposed at the distal portion such that the fiducial coil axis is orthogonal to the longitudinal axis of the endoscope.

16. The endoscope as claimed in claim 15 further comprising means for tracking movement of the r.f. receive coil and means for correcting magnetic resonance image artifacts due to the movement of the r.f. receive coil.

17. A method of reducing artifacts in magnetic resonance imaging when utilizing an endoscope, said method comprising:
    inserting an endoscope into a subject, the endoscope comprising a distal portion, a steerable flexible portion connected to the distal portion, an r.f receive coil disposed at the distal portion, a fiducial marker disposed at the distal portion in a fixed spatial relationship to the r.f. receive coil, and a fiducial r.f coil surrounding the fiducial marker;
    collecting magnetic resonance image data of a subject with the r.f receive coil;
    monitoring motion of the r.f. receive coil with the fiducial r.f. coil and marker; and
    adjusting the magnetic resonance image data using the monitored motion of the r.f. receive coil.

18. The method as claimed in claim 17 wherein the distal portion comprises non-metallic material and the steerable flexible portion comprises non-metallic material.

* * * * *